(12) United States Patent
Muller

(10) Patent No.: US 9,421,283 B2
(45) Date of Patent: *Aug. 23, 2016

(54) KIT AND METHOD FOR PRODUCING A RADIOPHARMACEUTICAL

(71) Applicant: ZENTRALKLINIK BAD BERKA GMBH, Bad Berka (DE)

(72) Inventor: Dirk Muller, Milda (DE)

(73) Assignee: ZENTRALKLINIK BAD BERKA GMBH, Bad Berka (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/402,036

(22) PCT Filed: May 14, 2013

(86) PCT No.: PCT/EP2013/059895
§ 371 (c)(1),
(2) Date: Nov. 18, 2014

(87) PCT Pub. No.: WO2013/171188
PCT Pub. Date: Nov. 21, 2013

(65) Prior Publication Data
US 2015/0133634 A1    May 14, 2015

(30) Foreign Application Priority Data

May 18, 2012 (DE) .......................... 10 2012 208 375

(51) Int. Cl.
| | | |
|---|---|---|
| C07K 1/13 | (2006.01) | |
| C07F 19/00 | (2006.01) | |
| B01L 3/00 | (2006.01) | |
| C07F 5/00 | (2006.01) | |
| A61K 51/08 | (2006.01) | |

(52) U.S. Cl.
CPC ................ *A61K 51/083* (2013.01); *C07K 1/13* (2013.01)

(58) Field of Classification Search
None
See application file for complete search history.

(56) References Cited

U.S. PATENT DOCUMENTS

| 7,011,816 | B2 | 3/2006 | Griffiths et al. | |
|---|---|---|---|---|
| 8,147,804 | B2 | 4/2012 | Roesch et al. | |
| 2003/0176784 | A1* | 9/2003 | Griffiths ............. | A61K 51/1093 600/431 |
| 2008/0277350 | A1 | 11/2008 | Roesch et al. | |

FOREIGN PATENT DOCUMENTS

| CA | 2816070 | 11/2013 |
|---|---|---|
| DE | 102004057225 | 6/2006 |
| WO | 2006056395 | 6/2006 |
| WO | 2009102378 | 8/2009 |
| WO | 2011106846 | 9/2011 |

OTHER PUBLICATIONS

Mueller et al. Bioconjugate Chemistry Aug. 15, 2012, vol. 23, No. 8, p. 1712-1717, "Simplified NaCl Based 68Ga Concentration and Labeling Procedure for Rapid Synthesis of 68Ga Radiopharmaceuticals in High Radiochemical Purity."
Schultz et al. Applied Radiation and Isotopes Jun. 1, 2013, vol. 76, p. 46-54, "A new automated NaCl based robust method for routine production of gallium-68 labeled peptides."
Velikyan., Medicinal Chemistry Sep. 1, 2011, vol. 7, No. 5, p. 345-379, "Positron Emitting [68 Ga]Ga-Based Imaging Agents: Chemistry and Diversity."
Velikyan., Digital Comprehensive Summaries of Uppsala Dissertations From the Faculty of Science and Technology 73, 2005, 70 Pages, "Synthesis, Characterisation and Application of 68Ga-labelled Macromolecules."
International Search Report for PCT/EP2013/059895, English translation attached to original, Both completed by the European Patent Office on Jul. 16, 2013, All together 7 Pages.
Canadian Office Action for Canadian Application No. CA 2873711, Completed by the Canadian Intellectual Property Office, Dated Mar. 21, 2016, 5 Pages.
Liu et al. Bioconjugate Chem. 2003, vol. 14, p. 1052-1056, "Ascorbic Acid:? Useful as a Buffer Agent and Radiolytic Stabilizer for Metalloradiopharmaceuticals".
Decristoforo et al. Nuclear Medicine Communications 2007, vol. 28, p. 870-875, "A fully automated synthesis for the preparation of 68Ga-labelled peptides".
Breeman et al. Eur. J. Nucl. Med Mol Imaging 2005, vol. 32, p. 478-485, "Radiolabelling DOTA-peptides with 68Ga".
Sigma-Aldrich Bulletin 862-TSK-GEL Nonporous Resin Columns1996, 8 Pages, "TSK-GEL Nonporous Resin Columns for Rapid Analysis of Proteins, Peptides, and Nucleic Acids".
Muller et al. World Journal of Nuclear Medicine Jun. 2011, vol. 10, Issue 1, 4 Pages, "A New High Efficient NaCl Based Cationic 68Ge/68Ga Generator Eluate Purification".
Muller et al. World Journal of Nuclear Medicine Jun. 2011, vol. 10, Issue 1, 4 Pages, "A New Synthesis Pathway and Quality Control of 68-Ga-BPAMD for Clinical Application".
Muller et al. Theranostics Gallium-68, and Other Radionuclides, A Pathway to Personalized Diagnosis and Treatment 2011, 11 Pages, "Purification and Labeling Strategies for 68Ga from 68Ge/68Ga Generator Eluate".

* cited by examiner

*Primary Examiner* — Marcela M Cordero Garcia
*Assistant Examiner* — Catherine Mader
(74) *Attorney, Agent, or Firm* — Brooks Kushman P.C.

(57) ABSTRACT

A kit for producing a radiopharmaceutical, having: a cation exchange cartridge; a reaction vial having a marker precursor; a solution vial having a solvent; an elution vial having a sterile solution including common salt (NaCl) and hydrochloric acid (HCl); and a buffer salt. A method for producing a radiopharmaceutical is also disclosed.

14 Claims, 1 Drawing Sheet

KIT AND METHOD FOR PRODUCING A RADIOPHARMACEUTICAL

CROSS-REFERENCE TO RELATED APPLICATION

This application is the U.S. national phase of PCT Application No. PCT/EP2013/059895 filed on May 14, 2013, which claims priority to DE Patent Application No. 10 2012 208 375.8 filed on May 18, 2012, the disclosures of which are incorporated in their entirety by reference herein.

The invention relates to a kit and to a method for producing a radiopharmaceutical.

Imaging techniques for medical diagnosis are commonplace, and in some cases have been so for decades. In some of these techniques, examples being positron emission spectroscopy (PET) or single photon emission computer tomography (SPECT), peptides, as for example edotreotide (DOTATOC), are labeled with radionuclides, as for example $^{68}$gallium, and used as radiopharmaceuticals, also called tracers. Within the human body, the radiopharmaceutical binds to particular receptors, which especially in the case of tumor cells are overexpressed. By means of the imaging techniques, the elevated beta-plus decay of the $^{68}$gallium can be ascertained and localized. According to [I. Velikyan: *Synthesis, Characterisation and Application of $^{68}$Ga-labelled Macromolecules*. Dissertation, Uppsala University, 2005], the $^{68}$gallium isotope decays with a half-life of 67.629 minutes to an extent of 89% with emission of a positron with at most 1.9 MeV, and to an extent of 11% with electron capture; the product in each case is the stable isotope $^{68}$zinc. In nuclear medicine application, the positron which has been emitted collides with an electron after a few millimeters, with which it breaks down to form two photons each with 511 keV, the two photons being irradiated from the annihilation site at an angle of virtually 180° from one another. The irradiated photons can be detected with appropriate detectors, and the location of the annihilation can be determined very precisely by reconstruction of a plurality of detection events.

In view of the short half-life of $^{68}$gallium, the radiopharmaceutical cannot be held for a prolonged time, but must instead be prepared a relatively short time prior to the intended use.

$^{68}$Gallium is generated by what are called gallium-68 generators, also called $^{68}$Ge/$^{68}$Ga generators, from $^{68}$germanium. $^{68}$Germanium has a half-life of 270.8 days and decays into $^{68}$gallium. This accumulates in the generator to a concentration governed by its own decay. The $^{68}$gallium formed is separated from the stationary phase of the $^{68}$germanium mother nuclide by means of a solvent which is introduced into the generator and with which only gallium, but not germanium, is eluted.

In known methods, hydrochloric acid with a normality of 0.05 N to 0.4 N is used for the eluting. The elution volume in this case is between 5 ml and 10 ml. The eluate, accordingly, contains hydrochloric acid and cannot be used directly to label peptides.

A variety of solutions have been disclosed for this problem.

In the case of the method of anionic concentration, the eluate is admixed with a large volume of concentrated hydrochloric acid, the $^{68}$Ga is collected by means of an anion exchanger, and it is then eluted with water into a HEPES buffer solution (2-(4-(2-hydroxyethyl)-1-piperazinyl)ethanesulfonic acid) for the labeling of, for example, peptides. With this method, subsequent purification of the product is required, in other words the removal of unwanted substances. Moreover, large quantities of hydrochloric acid must be used.

Also known is combined cationic/anionic concentration, in which case two different cartridges are used for the cation exchange (SCX—strong cation exchanger) and for the anion exchange (SAX—strong anion exchanger).

With the cationic concentration method, the $^{68}$gallium is held on a cation exchanger (SCX) and then eluted with an acetone/hydrochloric acid solution. The product obtained therefore comprises acetone, which, prior to use in the human body, must be removed by distillation at temperatures above 90° C. In order to verify complete removal of the acetone, intensive quality control is required, by means of a gas chromatograph, for example.

It is an object of the invention to specify a kit for the improved production of a radiopharmaceutical, and also to specify a corresponding improved method.

The object is achieved in accordance with the invention by a kit having the features of claim 1 and by a method having the features of claim 13.

Advantageous embodiments of the invention are subject matter of the dependent claims.

A kit of the invention comprises:
  a sterile cation exchange cartridge (SCX cartridge),
  a reaction vial with a labeling precursor, more particularly
    a lyophilized labeling precursor,
  a solution vial with a solvent, such as a sterile aqueous
    solution of acetic acid and hydrochloric acid,
  an elution vial with sterile sodium chloride/hydrochloric
    acid solution,
  a buffer salt.

A vial may also be termed an ampoule or septum bottle.

The buffer salt may be present, for example, in the reaction vial or in the solution vial.

The contents of the reaction vial have preferably been lyophilized.

Additionally provided in the reaction vial may be lyophilized ascorbic acid or another suitable stabilizer. The stabilizer prevents radiolytic degradation of the labeled substance during the use of the radiopharmaceutical.

As buffer salt, for example, ammonium acetate or sodium acetate may be used.

The kit is used as follows:

A $^{68}$Ge/$^{68}$Ga generator provides the $^{68}$gallium needed for labeling. The $^{68}$Ge/$^{68}$Ga generator is eluted using hydrochloric acid, with a concentration of 0.1 mol/l, for example. In this way, $^{68}$gallium is eluted. The generator eluate is supplied to the SCX cartridge. The SCX cartridge used may be, for example, a silica gel-based (silica based) cartridge. The SCX cartridge is preconditioned, for example, with 1 ml of hydrochloric acid of 5.5 mol/l concentration, and 10 ml of water. The preferably lyophilized mixture in the reaction vial is dissolved with the solvent from the solution vial. The SCX cartridge is then eluted, using the solution from the elution vial, into the reaction vial.

The reaction solution which is produced in the reaction vial may optionally be heated at 90° C. to 100° C., over a time of 5 minutes to 15 minutes, for example, more particularly seven minutes, in order to accelerate the reaction, in which the $^{68}$gallium joins with the labeling precursor to form the tracer. The reaction may also take place at room temperature, in which case a correspondingly greater amount of time may be needed.

The concentration of unbound $^{68}$gallium is preferably smaller than 5%. The radiochemical purity of the tracer is greater than 95%. The reaction mixture contains no toxic or objectionable substances, and so there is no need for subsequent purification. After sterile filtration, carried out optionally, the radiochemical yield is around 82% (n.d.c.—non decay corrected).

At the end of the reaction, the radiopharmaceutical may be neutralized by addition of a sterile phosphate buffer, an example being 2 ml of sodium phosphate, 1 mmol/ml $Na^+$, 0.6 mmol/ml $PO_4^{3-}$, pH 7.0.

Quality control by thin-layer chromatography may then follow. The tracer thus produced can be used subsequently, without further purification, as a radiopharmaceutical.

The kit of the invention can be used for routinely available application in clinical practice in the context of $^{68}$Ga labeling procedures. The kit of the invention reduces the level of operation with concentrated hydrochloric acid during the purifying and concentrating procedure on the $^{68}$Ga eluate. The attainable end product (tracer) is available with high purity and in a high yield of around 80% to 95%. As a result, it is likewise possible to avoid the use of acetone or other organic solvents or compounds such as 2-(4-(2-hydroxyethyl)-1-piperazinyl)ethanesulfonic acid (HEPES). In this way, there is also no need, relative to methods known from the prior art, for verification that the acetone has been removed completely, and so there is no requirement for intensive quality control, by means of a gas chromatograph, for example. In this way, it is made possible to produce kits which can be employed by medical staff in a relatively simple way, by adding the solution to the lyophilized mixture, without any need for costly and complicated laboratory equipment.

The tracers obtained are stable for longer than tracers known from the prior art, allowing multi-dose products to be produced for the labeling and investigation of a number of patients.

In one embodiment of the invention, the reaction vial contains a lyophilized mixture of sodium acetate and a ligand-conjugated peptide, as for example DOTA-(1,4,7,10-tetraazacyclododecane-1,4,7,10-tetraacetic acid) or NODAGA-conjugated peptide, more particularly DOTATOC (edotreotide) or DOTATATE (DOTA-[Tyr$^3$]octreotate). The tracer thus formed can be used in particular for the diagnosis of neuroendocrine tumors by means of positron emission tomography.

Instead of sodium acetate, ammonium acetate may be used in principle, but sodium acetate is more suitable for lyophilization.

In one embodiment of the invention, the reaction vial contains:
  at most 1 mg, preferably 15 µg to 100 µg, of the conjugated peptide,
  20 mg to 40 mg, preferably 27.6 mg, of buffer salt, more particularly sodium acetate,
  at most 100 mg, preferably at most 5 mg, of L-ascorbic acid.

In one embodiment of the invention, the solution vial contains:
  1 ml to 10 ml of water and also hydrochloric acid and acetic acid in an amount such that the pH of the solution composed of the contents of the reaction vial, the solvent from the solution vial, and the elution vial solution used to elute the SCX cartridge is between 3 and 4.

In one embodiment of the invention, the solution vial contains:
  1 ml to 10 ml, preferably 1 ml to 3 ml, of water
  2 µl to 10 µl, preferably 6.73 µl, of concentrated hydrochloric acid
  2 µl to 10 µl, preferably 4 µl to 8 µl, of acetic acid.

In one embodiment of the invention, the elution vial contains 0.25 ml to 3 ml, preferably 0.5 ml, of elution solution composed of 5 mol/l sodium chloride and 5.5 mol/l hydrochloric acid with 10 µl to 100 µl, preferably 25 µl, of 5.5 mol/l hydrochloric acid per ml of 5 mol/l sodium chloride. The SCX cartridge is preferably eluted with 0.5 ml of the NaCl/HCl elution solution.

A method of the invention for producing a radiopharmaceutical comprises the following steps:
  obtaining a generator eluate comprising $^{68}$gallium from a $^{68}$Ge/$^{68}$Ga generator by means of hydrochloric acid,
  passing the generator eluate into a cation exchange cartridge in which the $^{68}$gallium is held,
  removing an effluent of the generator eluate from the cation exchange cartridge,
  eluting the $^{68}$gallium from the cation exchange cartridge by means of a solution comprising sodium chloride and hydrochloric acid and passing it into a mixture of a labeling precursor and sodium acetate.

In one embodiment, the method may be carried out by means of the kit of the invention.

Working examples of the invention are elucidated in more detail below with reference to drawings.

In these drawings.

Parts corresponding to one another bear the same reference numerals in all the figures.

Figure 1:
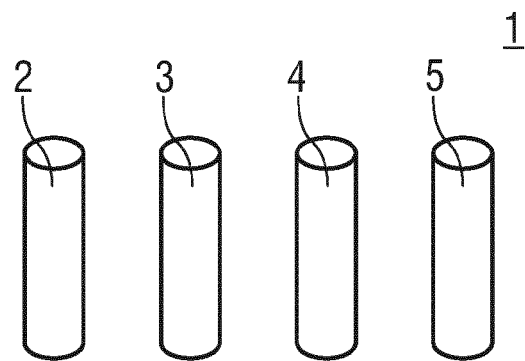
FIG. 1 shows a schematic view of a kit for producing a radiopharmaceutical.

FIG. 1 shows a schematic view of a kit 1 for producing a radiopharmaceutical. The kit 1 comprises:
  a cation exchange cartridge 2,
  a reaction vial 3 with a mixture comprising a labeling precursor and a buffer salt,
  a solution vial 4 with a solvent,
  an elution vial 5 with a sterile solution comprising sodium chloride NaCl and hydrochloric acid HCl.

The labeling precursor present in the reaction vial 3 is a DOTA- or NODAGA-conjugated peptide, more particularly DOTATOC or DOTATATE.

The mixture in the reaction vial 3 has been lyophilized.

The mixture in the reaction vial 3 optionally comprises ascorbic acid $C_6H_8O_6$ or another radical scavenger.

The solvent is preferably formed as an aqueous solution from acetic acid $C_2H_4O_2$ and hydrochloric acid HCl.

As the buffer salt, ammonium acetate $CH_3COONH_4$ or sodium acetate $C_2H_3NaO_2$ is provided.

The cation exchange cartridge 2 may be preconditioned with hydrochloric acid HCl and water $H_2O$, in particular with 1 ml of hydrochloric acid HCl of concentration 5.5 mol/l and 10 ml of water $H_2O$.

The reaction vial 3 contains:
  at most 1 mg, preferably 15 µg to 100 µg, of the conjugated peptide,
  20 mg to 40 mg, preferably 27.6 mg, of buffer salt, more particularly sodium acetate $C_2H_3NaO_2$,
  at most 100 mg, preferably at most 5 mg, of L-ascorbic acid $C_6H_8O_6$.

The solution vial 4 contains:
  ml to 10 ml, preferably 1 ml to 3 ml, of water $H_2O$
  2 µl to 10 µl, preferably 6.73 µl, of concentrated hydrochloric acid HCl
  2 µl to 10 µl, preferably 4 µl to 8 µl, of acetic acid $C_2H_4O_2$.

The elution vial 5 contains an amount of 0.25 ml to 3 ml of elution solution composed of 5 mol/l sodium chloride NaCl and 5.5 mol/l hydrochloric acid HCl with 10 µl to 100 µl, preferably 25 µl, of 5.5 mol/l hydrochloric acid HCl per ml of 5 mol/l sodium chloride NaCl.

The kit 1 may additionally comprise a vial with a neutralizing buffer, more particularly a sodium phosphate buffer.

Figure 2:
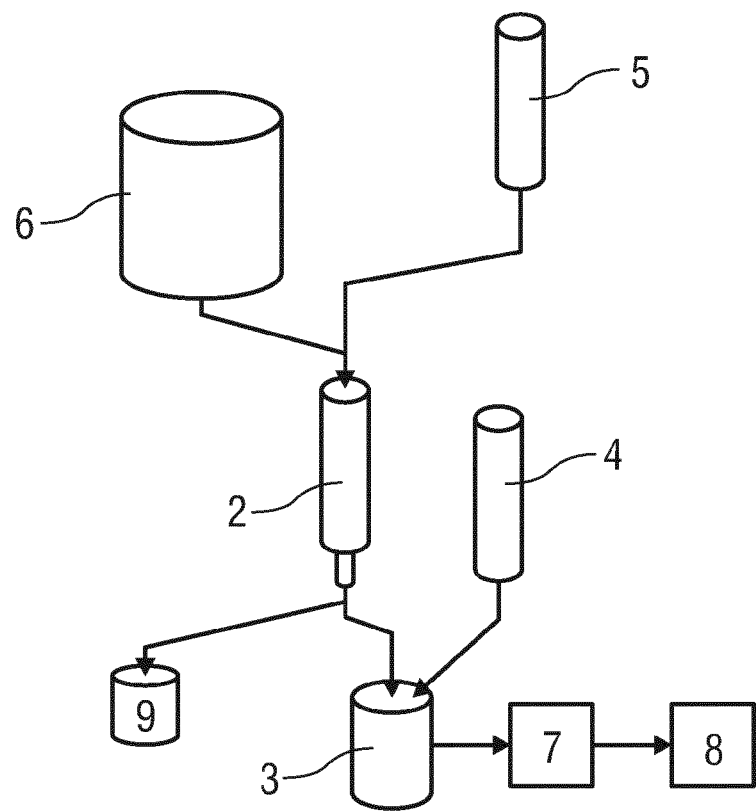
FIG. 2 shows an arrangement for producing a radiopharmaceutical by means of the kit.

FIG. 2 shows an arrangement for producing a radiopharmaceutical 8 by means of the kit 1.

A $^{68}$Ge/$^{68}$Ga generator 6 provides the $^{68}$gallium needed for labeling. The $^{68}$Ge/$^{68}$Ga generator 6 is eluted using hydrochloric acid HCl, with a concentration of 0.1 mol/l, for example. In this way, $^{68}$gallium is eluted and is held on the cation exchange cartridge 2. The generator eluate is supplied to the cation exchange cartridge 2. The 0.1 mol/l HCl effluent, possibly with traces of the $^{68}$germanium mother nuclide, is collected separately in a waste collecting vessel 9, and disposed of in line with the statutory provisions. The lyophilized mixture in the reaction vial 3 is dissolved with the solvent from the solution vial 4. The cation exchange cartridge 2 is then eluted by means of the solution from the elution vial 5 into the reaction vial 3.

The reaction solution which is produced in the reaction vial 3 may optionally be heated at 90° C. to 100° C., over a time of 5 minutes to 15 minutes, for example, more particularly seven minutes, in order to accelerate the reaction, in which the $^{68}$gallium joins with the labeling precursor to form the radiopharmaceutical 8, also called tracer. The reaction may also take place at room temperature, in which case it requires a correspondingly greater amount of time.

At the end of the reaction, a sterile phosphate buffer may be added.

The reaction product may optionally be filtered using a sterile filter 7.

The tracer thus produced can then be used as radiopharmaceutical 8.

LIST OF REFERENCE NUMERALS

1 Kit
2 Cation exchange cartridge
3 Reaction vial
4 Solution vial
5 Elution vial
6 $^{68}$Ge/$^{68}$Ga generator
7 Sterile filter
8 Radiopharmaceutical
9 Waste collecting vessel

The invention claimed is:

1. A kit for producing a radiopharmaceutical, comprising:
a cation exchange cartridge,
a reaction vial with a ligand-conjugated peptide as labeling precursor,
a solution vial with a solvent formed from an aqueous solution of acetic acid ($C_2H_4O_2$) and hydrochloric acid (HCl),
an elution vial with a sterile solution comprising sodium chloride (NaCl) and hydrochloric acid (HCl), and
a buffer salt.

2. The kit as claimed in claim 1, wherein the buffer salt is present in the reaction vial or in the solution vial.

3. The kit as claimed in claim 1, wherein a DOTA- or NODAGA-conjugated peptide, is present as the ligand-conjugated peptide.

4. The kit as claimed in claim 1, wherein the contents of the reaction vial have been lyophilized.

5. The kit as claimed in claim 1, wherein ascorbic acid ($C_6H_8O_6$) is present in the reaction vial.

6. The kit as claimed in claim 1, wherein ammonium acetate ($CH_3COONH_4$) or sodium acetate ($C_2H_3NaO_2$) is provided as buffer salt.

7. The kit as claimed in claim 1, wherein the reaction vial contains:
at most 1 mg, of the conjugated peptide,
20 mg to 40 mg, of buffer salt, and
at most 100 mg, of L-ascorbic acid ($C_6H_8O_6$).

8. The kit as claimed in claim 1, wherein the solution vial contains:
1 ml to 10 ml, of water ($H_2O$)
2 µl to 10 µl, of concentrated hydrochloric acid (HCl)
2 µl to 10 µl, of acetic acid ($C_2H_4O_2$).

9. The kit as claimed in claim 1, wherein the elution vial contains 0.25 ml to 3 ml of elution solution composed of 5 mol/l sodium chloride (NaCl) and 5.5 mol/l hydrochloric acid (HCl) with 10 µl to 100 µl, of 5.5 mol/l hydrochloric acid (HCl) per ml of 5 mol/l sodium chloride (NaCl).

10. The kit as claimed in claim 1, further comprising a vial with a neutralizing buffer.

11. A method for producing a radiopharmaceutical, comprising the following steps:
obtaining a generator eluate comprising $^{68}$gallium from a $^{68}$Ge/$^{68}$Ga generator by means of hydrochloric acid (HCl),
passing the generator eluate into a cation exchange cartridge in which the $^{68}$gallium is held,
removing an effluent of the generator eluate from the cation exchange cartridge, and
eluting the $^{68}$gallium from the cation exchange cartridge by means of a solution comprising sodium chloride (NaCl) and hydrochloric acid (HCl) and passing it into a mixture of a ligand-conjugated peptide as labeling precursor and sodium acetate ($C_2H_3NaO_2$).

12. The kit as claimed in claim 1, wherein DOTATOC or DOTATATE, is present as the ligand-conjugated peptide.

13. The kit as claimed in claim 1, wherein the reaction vial contains:
at most 15 µg to 100 µg, of the conjugated peptide,
20 mg to 40 mg, of sodium acetate ($C_3H_3NaO_2$), and
at most 5 mg, of L-ascorbic acid ($C_6H_8O_6$).

14. The kit as claimed in claim 1, wherein the solution vial contains:
1 ml to 3 ml, of water ($H_2O$),
2 µl to 10 µl, of concentrated hydrochloric acid (HCl), and
4 µl to 8 µl, of acetic acid ($C_2H_4O_2$).

* * * * *